United States Patent
Scott et al.

(10) Patent No.: US 10,370,682 B2
(45) Date of Patent: *Aug. 6, 2019

(54) XYLANASE VARIANTS AND POLYNUCLEOTIDES ENCODING SAME

(71) Applicant: NOVOZYMES A/S, Bagsvaerd (DK)

(72) Inventors: Brian R. Scott, West Sacramento, CA (US); Mark David Wogulis, Davis, CA (US); Sven Pedersen, Gentofte (DK); James Lavigne, Wake Forest, NC (US)

(73) Assignee: NOVOZYMES A/S, Bagsvaerd (DE)

( * ) Notice: Subject to any disclaimer, the term of this patent is extended or adjusted under 35 U.S.C. 154(b) by 208 days.

This patent is subject to a terminal disclaimer.

(21) Appl. No.: 15/315,539

(22) PCT Filed: Jun. 25, 2015

(86) PCT No.: PCT/US2015/037732
§ 371 (c)(1),
(2) Date: Dec. 1, 2016

(87) PCT Pub. No.: WO2015/200659
PCT Pub. Date: Dec. 30, 2015

(65) Prior Publication Data
US 2017/0096687 A1    Apr. 6, 2017

(30) Foreign Application Priority Data
Jun. 25, 2014 (EP) .................................... 14173811

(51) Int. Cl.
| | | |
|---|---|---|
| C12P 19/14 | (2006.01) | |
| C12N 9/24 | (2006.01) | |
| C12P 19/34 | (2006.01) | |
| C12P 21/06 | (2006.01) | |
| C12N 1/20 | (2006.01) | |
| C12P 7/10 | (2006.01) | |
| C12N 15/52 | (2006.01) | |
| C12N 15/82 | (2006.01) | |

(52) U.S. Cl.
CPC .............. *C12P 7/10* (2013.01); *C12N 9/2402* (2013.01); *C12N 9/248* (2013.01); *C12N 9/2482* (2013.01); *C12N 15/52* (2013.01); *C12N 15/8257* (2013.01); *C12Y 302/01008* (2013.01); *C12Y 302/01037* (2013.01); *Y02E 50/16* (2013.01)

(58) Field of Classification Search
CPC ....................................................... C12N 9/24
See application file for complete search history.

(56) References Cited

U.S. PATENT DOCUMENTS 7,759,102 B2 * 7/2010 Van Den Hombergh ...................
                                                              A21D 8/042
                                                              435/200
9,637,727 B2 * 5/2017 Spodsberg ........... C12N 9/2482
2014/0322764 A1  10/2014 Yannai

FOREIGN PATENT DOCUMENTS

| EP | 0695349 B1 | 7/1996 |
| EP | 2784161 A1 | 10/2014 |
| WO | 03/020923 A1 | 3/2003 |
| WO | 2006/078256 A2 | 7/2006 |

OTHER PUBLICATIONS

Cheeseman et al., UniProt Databaase, accession No. W6QUB1, Apr. 2014.*
Detroym , 1981, Organic Chemicals from Biomass, 19-41.
Juge et al, 2004, Biochimica et Biophysica Acta Prot Proteomics 1696 (2), 203-211.
Paice et al, 1984, J Wood Chem Technol 4, 187-198.
Pommier et al, 1989, Tappi J, 187-191.
Senior et al, 1988, Biotech Lett 10 (12), 907-912.
Tahir et al, 2002, J Biol Chem 277 (46), 44035-44043.
Tahir et al, 2004, FEMS Microbiol Lett 239 (1), 9-15.
Visser et al, 1992, Progress Biotechnol, 1-17 & 50-67.

* cited by examiner

*Primary Examiner* — Maryam Monshipouri
(74) *Attorney, Agent, or Firm* — David Fazzolare

(57) ABSTRACT

The present invention relates to xylanase variants, comprising an alteration at least at one position corresponding to position 87 of the polypeptide of SEQ ID NO: 3, wherein the variant has xylanase activity and has increased xylanase inhibitor tolerance compared to the xylanase of SEQ ID NO: 3; and i) wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3; or ii) wherein the number of alterations is 1-20, e.g., 1-10 such as 1, 2, 3, 4, 5, 6, 7, 8, 9 or 10 alterations. The present invention also relates to polynucleotides encoding the variants; nucleic acid constructs, vectors, and host cells comprising the polynucleotides; and methods of using the variants.

17 Claims, 4 Drawing Sheets

Specification includes a Sequence Listing.

XYLANASE VARIANTS AND POLYNUCLEOTIDES ENCODING SAME

CROSS-REFERENCE TO RELATED APPLICATIONS

This application is a 35 U.S.C. 371 national application of PCT/US2015/037732 filed Jun. 25, 2015, which claims priority or the benefit under 35 U.S.C. 119 of European application no. 14173811.2 filed Jun. 25, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to xylanase variants, polynucleotides encoding the variants, methods of producing the variants, and methods of using the variants.

Description of the Related Art

Plant cell wall polysaccharides constitute approximately 90% of the plant cell wall and can be divided into three groups: cellulose, hemicellulose, and pectin. Cellulose represents the major constituent of call wall polysaccharides. Hemicelluloses are the second most abundant constituent of plant cell walls. The major hemicellulose polymer is xylan.

Xylan is a polymer of D-xylose linked by beta-1,4-xylosidic bonds. Xylan can be degraded to xylose and xylo-oligomers by acid or enzymatic hydrolysis. Enzymatic hydrolysis of xylan produces free sugars without the by-products formed with acid (e.g., furans).

Enzymes capable of degrading xylan and other plant cell wall polysaccharides are important for the food industry, primarily for baking and in fruit and vegetable processing such as fruit juice production or wine making, where their ability to catalyze the degradation of the backbone or side chains of the plant cell wall polysaccharide is utilized (Visser et al., *Xylans and Xylanases*, Proceedings of an International Symposium, Wageningen, The Netherlands, Elsevier Science Publishers, 1992). The biodegradation of the xylan backbone depends on two classes of enzymes: endoxylanases and beta-xylosidases. Endoxylanases (EC 3.2.1.8) cleave the xylan backbone into smaller oligosaccharides, which can be further degraded to xylose by beta-xylosidases (EC 3.2.1.37). Other enzymes involved in the degradation of xylan include, for example, acetylxylan esterase, arabinase, alpha-glucuronidase, ferulic acid esterase, and p-coumaric acid esterase.

Other applications for xylanases are enzymatic breakdown of agricultural wastes for production of alcohol fuels, enzymatic treatment of animal feeds for hydrolysis of pentosans, manufacturing of dissolving pulps yielding cellulose, and bio-bleaching of wood pulp [Detroym R. W. In: Organic Chemicals from Biomass, (CRC Press, Boca Raton, Fla., 1981) 19-41; Paice and Jurasek, *J. Wood Chem. Technol.* 4: 187-198; Pommier and Fuentes, 1989, *Tappi Journal* 187-191; Senior et al., 1988, *Biotechnol. Letters* 10: 907-9121].

Xylan is abundant in plant cell walls. Arabinoxylan, in particular, is abundant in grains, such as wheat, barley and rye. Soluble forms of arabinoxylan render aqueous mashes of these grains highly viscous. Xylanases break down (arabino)xylan and release short chain, soluble sugars. Xylanases, such as those from GH Family 5, 8, 10 and/or 11, may be used in bioethanol applications to reduce viscosity and improve yields of fermentable sugars. However, cereal grains produce inhibitor proteins that bind many microbial xylanases rendering them ineffective.

EP695349 discloses a GH10 xylanase from *Aspergillus aculeatus*.

WO2006/078256 discloses a GH10 xylanase from *Aspergillus fumigatus*.

The present invention provides variants of a xylanase with improved properties compared to its parent enzyme.

SUMMARY OF THE INVENTION

In particular the present invention provides a variant of the *Aspergillus fumigatus* wild type xylanase disclosed in WO 2006/078256 having improved inhibitor tolerance compared to the wild type enzyme.

The present invention relates to a xylanase variant, comprising an alteration at least at one position corresponding to position 87 of the polypeptide of SEQ ID NO: 3, wherein the variant has xylanase activity and has increased xylanase inhibitor tolerance compared to the xylanase of SEQ ID NO: 3; and
i) wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3; or
ii) wherein the number of alterations is 1-20, e.g., 1-10 such as 1, 2, 3, 4, 5, 6, 7, 8, 9 or 10 alterations.

The present invention also relates to isolated polynucleotides encoding the variants; nucleic acid constructs, vectors, and host cells or transgenic plants comprising the polynucleotides; and methods of producing the variants.

Another aspect of the invention relates to a process of producing a fermentation product from starch-containing material comprising the steps of: (a) liquefying starch-containing material in the presence of an alpha amylase; (b) saccharifying the liquefied material; and (c) fermenting with a fermenting organism; wherein the xylanase variant of the invention is present during step (a).

Another aspect of the invention relates to a process of producing a syrup product from starch-containing material, comprising the step of: (a) blending the dry starch-containing material with water to form a mash, (b) liquefying starch-containing material in the presence of an alpha amylase; (c) saccharifying the liquefied material in the presence of a glucoamylase, wherein the xylanase variant of the invention is present during step (a) and/or (b).

Another aspect of the invention relates to a process for producing a fermentation product, comprising:

(a) saccharifying a cellulosic or xylan-containing material with an enzyme composition in the presence of the xylanase variant of the invention;

(b) fermenting the saccharified cellulosic or xylan-containing material with one or more fermenting microorganisms to produce the fermentation product; and (c) recovering the fermentation product from the fermentation.

Another aspect of the invention relates to a composition comprising the variant of the invention.

Another aspect of the invention relates to a process for degrading a xylan containing material, comprising: treating the xylan material with an enzyme composition of the invention.

Another aspect of the invention relates to a whole broth formulation or cell culture composition, comprising the variant of any of claims 1-7.

DEFINITIONS

Figure 1:
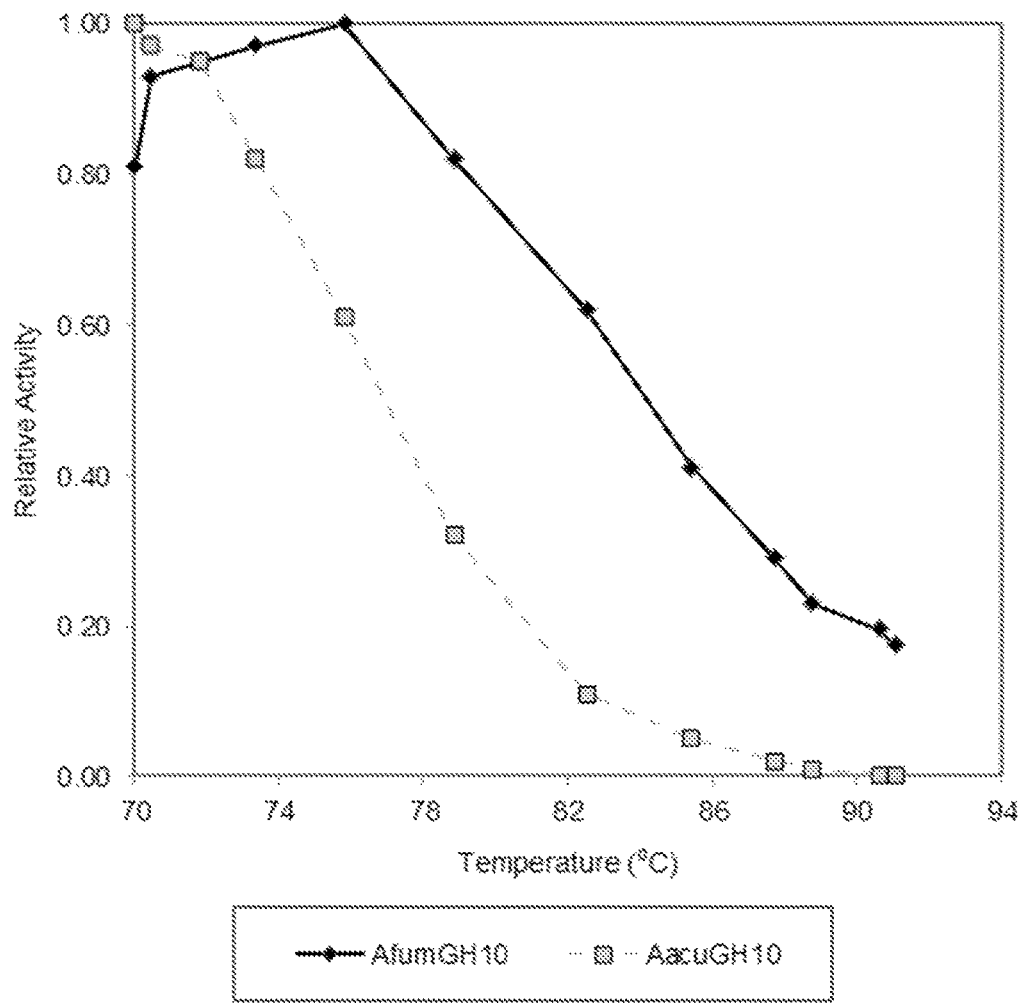
FIG. 1 shows thermoactivity profiles of GH10 xylananses from *Aspergillus fumigatus* (AfumGH10) and *Aspergillus aculeatus* (AacuGH10). The xylanases were incubated with wheat arabinoxylan for 1 h at various temperatures in 50 mM sodium citrate, pH 5.0. Activity was measured using a DNS reducing sugar assay. Activities shown at each temperature are relative to the maximum activity for each xylanase. The *A. fumigatus* GH10 retains a far greater fraction of its maximum activity at higher temperatures indicating it is more thermoactive and/or more thermostable than the *A. aculeatus* GH10.

Xylanase Activity: The term "xylanase" is defined herein as a 1,4-beta-D-xylan-xylanohydrolase (E.C. 3.2.1.8) which catalyzes the endohydrolysis of 1,4-beta-D-xylosidic linkages in xylans. For purposes of the present invention, xylanase activity is determined with 0.5% wheat arabinoxylan in 100 mM sodium citrate buffer, pH 5.0 at 50° C. One unit of xylanase activity is defined as 1.0 μmole of xylose equivalents produced per minute at 50° C., pH 5.0 from 0.5% arabinoxylan as substrate in 100 mM sodium citrate, pH 5.0 buffer. In some cases xylanase activity is measured during higher temperature incubations with wheat arabinoxylan, conditions under which the xylanase may be inactivated during the assay. In this case, the activity is referred to as "apparent" xylanase activity. In one embodiment the polypeptides of the present invention have at least 75%, preferably at least 80%, more preferably at least 85%, even more preferably at least 90%, most preferably at least 95%, and even most preferably at least 100% of the xylanase activity of the polypeptide of SEQ ID NO: 3 further comprising the H87Y substitution, and wherein the variant xylanase has at least 75%, at least 80%, at least 85%, at least 90%, at least 95%, at least 96%, at least 97%, at least 98%, at least 99%, but less than 100% sequence identity to the polypeptide of SEQ ID NO: 3.

In one embodiment xylanase activity is determined as relative activity in the presence of xylanase inhibitors extracted from wheat as described in the examples.

The variant of the invention has an increase in relative xylanase activity over the wild type xylanase of at least a factor 7×, particularly 8×, particularly 8.5× more particularly 9×, in the presence of wheat xylanase inhibitors, particularly XIP-1, in amounts that will reduce the wild type xylanase activity to less than 10%.

Xylanase inhibitor: The term "xylanase inhibitor" is defined herein as inhibitor proteins produced in cereal grains (grasses whose seeds are used for food). In particular the cereal grain is wheat. More particularly the inhibitor proteins are selected from a group comprising Xylanase-Inhibiting Protein (XIP), *T. aestivum* Xylanase Inhibitor (TAXI) and Thaumatin-Like Xylanase Inhibitor (TLXI). Proteinaceous inhibitors of xylanases found in cereals other than wheat are similar in structure and properties to XIP and TAXI from wheat and referred to as XIP-type and TAXI-type proteins. XIP comprises a group of homologous proteins encoded by different genes, where XIP-I is most abundant. Similarly, TAXI is not a single protein but rather comprises two proteins, TAXI-I and TAXI-II. Furthermore, TAXI and TAXI-like inhibitors each have two isoforms that result from proteolytic processing of the mature protein. There are referred to as TAXI-IA, TAXI-IB, TAXI-IIA and TAXI-IIB. Even more particularly, the inhibitor proteins are selected from a group comprising XIP-I, TAXI-IA, TAXI-IB, TAXI-IIA, TAXI-IIB and TLXI from wheat and their homologues in other cereals.

Microbial xylanases differ in their sensitivity and specificity to XIP, TAXI and TLXI (reviewed by Gusakov, Biochemistry (Moscow), 2010). XIP-I, or XIP-I-type, inhibitors inhibit many fungal GH family 11 and 10 xylanases while they generally do not inhibit bacterial GH11 xylanases. Crystal structures of XIP-I in complex with a GH10 xylanase from *Aspergillus nidulans* and a GH11 xylanase from *Pencillium funiculosum* have been published (Payan et al., 1994). TAXI, or TAXI-type, proteins inhibit fungal and bacterial GH Family 11 xylanases but do usually not affect those from GH Family 10.

Family 10 or Family GH10 or GH10: The term "Family 10" or "Family GH10" or "GH10" is defined herein as a polypeptide falling into the glycoside hydrolase Family 10 according to Henrissat B., 1991, A classification of glycosyl hydrolases based on amino-acid sequence similarities, *Biochem. J*. 280: 309-316, and Henrissat and Bairoch, 1996, Updating the sequence-based classification of glycosyl hydrolases, *Biochem. J*. 316: 695-696.

Xylan-containing material: The term "xylan-containing material" is defined herein as any material comprising xylan as a constituent. Xylan is a plant cell wall polysaccharide containing a backbone of beta-1,4-linked xylose residues. Side chains of 4-O-methylglucuronic acid and arabinose are generally present in varying amounts, together with acetyl and feruloyl groups. Xylan is a major constituent of hemicellulose.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has xylanase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C. p Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. In a particular embodiment the improved property include increased xylanase inhibitor tolerance.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 397 of SEQ ID NO: 2. Amino acids 1 to 19 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. The mature polypeptide is disclosed herein as SEQ ID NO: 3.

Mature polypeptide coding sequence: The term "mature polypeptide coding sequence" means a polynucleotide that encodes a mature polypeptide having xylanase activity. In one aspect, the mature polypeptide coding sequence is nucleotides 58 to 1194 of SEQ ID NO: 1. Nucleotides 1 to 57 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent Xylanase: The term "parent" or "parent xylanase" means a xylanase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type Xylanase: The term "wild-type" xylanase means a xylanase expressed by a naturally occurring microorganism, such as a bacterium, yeast, or filamentous fungus found in nature.

Conventions for Designation of Variants

For purposes of the present invention, the mature polypeptide disclosed in SEQ ID NO: 3 is used to determine the corresponding amino acid residue in another xylanase. The amino acid sequence of another xylanase is aligned with the mature polypeptide disclosed in SEQ ID NO: 3, and based on the alignment, the amino acid position number corresponding to any amino acid residue in the mature polypeptide disclosed in SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another xylanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide disclosed in SEQ ID NO: 3 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195 | 195 195a 195b |
| G | G-K-A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to a xylanase variant, comprising an alteration at least at one position corresponding to position 87 of the polypeptide of SEQ ID NO: 3, wherein the variant has xylanase activity and has increased xylanase inhibitor tolerance compared to the xylanase of SEQ ID NO: 3; and i) wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3; or ii) wherein the number of alterations is 1-20, e.g., 1-10 such as 1, 2, 3, 4, 5, 6, 7, 8, 9 or 10 alterations.

SEQ ID NO: 3 is the mature polypeptide of SEQ ID NO: 2. The position numbers referred to herein correspond to the position numbers of SEQ ID NO: 3.

Variants

The present invention provides xylanase variants, comprising an alteration, in particular a substitution, at least at one position corresponding to position 87 of SEQ ID NO: 3, and wherein the variant have xylanase activity.

In one embodiment the variant is isolated.

In an embodiment, the alteration is a substitution. More particularly the amino acid present in a position corresponding to position 87 is substituted with Tyr (Y). In one embodiment the substitutions is H87Y.

The xylanase variants of the invention have improved properties compared to the parent enzyme. In particular the variants have increase xylanase inhibitor tolerance over the parent enzyme. The specific substitution has been shown herein to increase the xylanase inhibitor tolerance of the variant xylanase compared to the xylanase of SEQ ID NO: 3.

In one particular embodiment the xylanase inhibitor is inhibitor proteins, particularly proteins present in cereal grains. In one embodiment the cereal grain is wheat.

More particularly the inhibitor proteins are selected from a group comprising Xylanase-Inhibiting Protein (XIP), *T. aestivum* Xylanase Inhibitor (TAXI) and Thaumatin-Like Xylanase Inhibitor (TLXI). Proteinaceous inhibitors of xylanases found in cereals other than wheat are similar in structure and properties to XIP and TAXI from wheat and referred to as XIP-type and TAXI-type proteins. XIP comprises a group of homologous proteins encoded by different genes, where XIP-I is most abundant. Similarly, TAXI is not a single protein but rather comprises two proteins, TAXI-I and TAXI-II. Furthermore, TAXI and TAXI-like inhibitors each have two isoforms that result from proteolytic processing of the mature protein. There are referred to as TAXI-IA, TAXI-IB, TAXI-IIA and TAXI-IIB. Even more particularly, the inhibitor proteins are selected from a group comprising XIP-I, TAXI-IA, TAXI-IB, TAXI-IIA, TAXI-IIB and TLXI from wheat and their homologues in other cereals.

Thus in one embodiment the present invention relates to a xylanase variant, comprising at least a substitution at one position corresponding to position 87 of the polypeptide of SEQ ID NO: 3, wherein the variant has xylanase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3, and wherein the variant has increased xylanase inhibitor tolerance.

In one aspect, the number of alterations in the variants of the present invention is 1-20, e.g., 1-10 and 1-5, such as 1, 2, 3, 4, 5, 6, 7, 8, 9 or 10 alterations. In another aspect, the variant consists of a substitution at position corresponding to position 87 of SEQ ID NO: 3, particularly 87Y.

In another aspect, the variant alteration comprises or consists of a substitution at a position corresponding to position 87. In another aspect, the amino acid at a position corresponding to position 87 is substituted with Ala, Arg, Asn, Asp, Cys, Gln, Glu, Gly, Ile, Leu, Lys, Met, Phe, Pro, Ser, Thr, Trp, Tyr or Val, preferably with Tyr. In another aspect, the variant alteration comprises or consists of the substitution H87Y of the polypeptide of SEQ ID NO: 3.

The variants may further comprise one or more additional alterations at one or more (e.g., several) other positions.

It should be noted that for all of the disclosed specific variants such further variation could be introduced without affecting significantly the properties of the xylanase variants. In one aspect, the number of substitutions in the variants of the present invention in addition to the specific substitutions discussed herein is 1-20, e.g., 1-10 and 1-5, such as 1, 2, 3, 4, 5, 6, 7, 8, 9 or 10 substitutions.

Therefore the % identity of the variant polypeptide compared to the parent polypeptide of SEQ ID NO: 3 may be at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one particular embodiment the variants have xylanase activity, and comprise the H87Y substitution, and the variant has at least 85%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 90%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 91%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 92%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 93%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 94%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 95%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 96%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 97%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 98%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

In one particular embodiment the variants have xylanase activity, and comprise the H87Y substitution, and the variant has at least 99%, but less than 100%, sequence identity to the polypeptide of SEQ ID NO: 3, and wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In an embodiment, the variant has increased xylanase inhibitor tolerance compared to the parent enzyme.

In a particular embodiment, the xylanase variant of the invention has an increase in relative xylanase activity over the wild type xylanase of at least a factor 7×, particularly 8×, particularly 8.5× more particularly 9×, in the presence of wheat xylanase inhibitors, particularly XIP-1, in amounts that will reduce the wild type xylanase activity to less than 10%.

Parent Xylanase

The parent xylanase may be (a) a polypeptide having at least 75% sequence identity to the mature polypeptide of SEQ ID NO: 2; (b) a polypeptide encoded by a polynucleotide that hybridizes under medium-high stringency conditions with (i) the mature polypeptide coding sequence of SEQ ID NO: 1, or (ii) the full-length complement of (i); or (c) a polypeptide encoded by a polynucleotide having at least 70% sequence identity to the mature polypeptide coding sequence of SEQ ID NO: 1.

In an aspect, the parent has a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, which have xylanase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 3.

In another embodiment, the parent is an allelic variant of the mature polypeptide of SEQ ID NO: 2.

In another aspect, the parent is encoded by a polynucleotide that hybridizes under high stringency conditions, or very high stringency conditions with (i) the mature polypeptide coding sequence of SEQ ID NO: 1, (ii) the full-length complement of (i) (Sambrook et al., 1989, Molecular Cloning, A Laboratory Manual, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the parent is encoded by a polynucleotide having a sequence identity to the mature polypeptide coding sequence of SEQ ID NO: 1 of at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

In one aspect, the parent is an *Aspergillus* xylanase, e.g., the xylanase of SEQ ID NO: 2 or the mature polypeptide thereof.

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus sub-*

*tilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Sac-* charomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a variant, comprising: (a) cultivating a recombinant host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant. Thus in one aspect the invention relates to a whole broth formulation or cell culture composition, comprising the variant of the invention.

Compositions

The present invention also relates to compositions comprising a variant of the present invention. Preferably, the compositions are enriched in such a variant. The term "enriched" means that the xylanase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an alpha-galactosidase, alpha-glucosidase, aminopeptidase, alpha-amylase, beta-galactosidase, beta-glucosidase, beta-xylosidase, carbohydrase, carboxypeptidase, catalase, cellobiohydrolase, mylchym, chitinase, cutinase, cyclodextrin glycosyltransferase, deoxyribonuclease, endoglucanase, esterase, glucoamylase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or other xylanase.

In a particular embodiment the composition comprises the xylanase of the invention and an alpha amylase. Preferred are bacterial alpha-amylases, which typically are stable at temperatures used during liquefaction. In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be truncated so it has around 491 amino acids (compared to SEQ ID NO: 3 in WO 99/19467. Preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467. The bacterial alpha-amylase may also have a substitution in a position corresponding to S239 in the *Bacillus licheniformis* alpha-amylase shown in SEQ ID NO: 4 in WO 99/19467, or a S242 variant of the *Bacillus stearothermophilus* alpha-amylase of SEQ ID NO: 3 in WO 99/19467. In a preferred embodiment the alpha-amylase is selected from the group of *Bacillus stearomthermphilus* alpha-amylase variants:

I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A+Q89R+E129V+K177L+ R179E+Q254S+M284V; and
I181*+G182*+N193F+E129V+K177L+R179E+K220P+ N224L+S242Q+Q254S (using SEQ ID NO: 3 disclosed in WO 99/19467 for numbering).

In another particular embodiment the composition comprises the xylanase of the invention, an alpha amylase, and a thermostable protease. In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 with the following mutations:

D79L+S87P+A112P+D142L;
D79L+S87P+D142L; or
A27K+D79L+Y82F+S87G+D104P+A112P+A126V+ D142L.

In another embodiment the thermostable protease is derived from a strain of the bacterium *Pyrococcus*, such as a strain of *Pyrococcus furiosus* (pfu protease)

In an embodiment the protease is the one shown as SEQ ID NO: 1 in U.S. Pat. No. 6,358,726-B1.

In another particular embodiment the composition comprises the xylanase of the invention, an alpha amylase, a thermostable protease, and a thermostable glucoamylase. In a specific embodiment the thermostable glucoamylase is from a strain of the genus *Penicillium*, especially a strain of *Penicillium oxalicum*, in particular the *Penicillium oxalicum* glucoamylasedisclosed as SEQ ID NO: 2 in WO 2011/127802. In a preferred embodiment the glucoamylase is a variant of the *Penicillium oxalicum* glucoamylase disclosed as SEQ ID NO: 2 in WO 2011/127802 having a K79V substitution and described in WO 2013/036526.

The compositions may be prepared in accordance with methods known in the art and may be in the form of a liquid or a dry composition. For instance, the composition may be in the form of granulate or microgranulate. The variant may be stabilized in accordance with methods known in the art.

Examples are given below of preferred uses of the compositions of the invention. The dosage of the composition of the invention and other conditions under which the composition is used may be determined on the basis of methods known in the art.

Uses

A variant of the present invention may be used in several applications to degrade or convert a xylan-containing material comprising treating the material with the variant (see, for example, WO 2002/18561). Consequently, the present invention also relates to methods for degrading a xylan-containing material, comprising treating the xylan-containing material with such a polypeptide having xylanase activity. The dosage of the polypeptides of the present invention and other conditions under which the preparation is used may be determined on the basis of methods known in the art.

A preferred use of the variant of the invention is for viscosity reduction in a process for liquefying a starch-containing material. The sources of the starch containing material may be selected from whole grains, corns, wheat, barley, rye, milo, sago, cassava, tapioca, sorghum, rice, peas, beans, and sweet potatoes, or mixtures thereof, or cereals, or sugar-containing raw materials, such as molasses, fruit materials, sugar cane or sugar beet, potatoes.

Liquefaction is performed in the presence of at least an alpha amylase and the xylanase variant of the invention. Liquefaction may be followed by saccharification and optionally fermentation to generate a fermentation product, preferably ethanol.

In one aspect the invention relates to a process of producing a fermentation product from starch-containing material comprising the steps of: (a) liquefying starch-containing material in the presence of an alpha amylase; (b) saccharifying the liquefied material; and (c)

fermenting with a fermenting organism; wherein the xylanase variant of the invention is present during step (a).

Saccharification and fermentation may be performed simultaneously. The fermentation product is preferably alcohol, more preferably ethanol.

In another embodiment the invention relates to a process of producing a syrup product from starch-containing material, comprising the step of: (a) blending the dry starch-containing material with water to form a mash, (b) liquefying starch-containing material in the presence of an alpha amylase; (c) saccharifying the liquefied material in the presence of a glucoamylase, wherein the xylanase variant of the invention is present during step (a) and/or (b).

The starch containing material is preferably selected from cereal, i.e., grasses whose seeds are used as food. In a particular embodiment the starch-containing material is selected from wheat or barley. Most particularly wheat.

The variants of the present invention may also be used in lignocellulosic biomass degradation or conversion to fermentable sugars for the production of, for example, fuel, potable ethanol, and/or fermentation products (e.g., acids, alcohols, ketones, gases, and the like). The variants are preferably used in combination with other xylan degrading enzymes and a cellulase composition (endoglucanase(s), cellobiohydrolase(s), and beta-glucosidase(s)).

In another embodiment the invention relates to a process for producing a fermentation product, comprising:
(a) saccharifying a cellulosic or xylan-containing material with an enzyme composition in the presence of the polypeptide having xylanase activity of the invention;
(b) fermenting the saccharified cellulosic or xylan-containing material with one or more fermenting microorganisms to produce the fermentation product; and
(c) recovering the fermentation product from the fermentation.

In one aspect the composition further comprises one or more enzymes selected from the group consisting of an endoglucanase, a cellobiohydrolase, and a beta-glucosidase.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The invention is further defined in the following paragraphs:

Paragraph [1]. A xylanase variant, comprising an alteration at least at one position corresponding to position 87 of the polypeptide of SEQ ID NO: 3, wherein the variant has xylanase activity and has increased xylanase inhibitor tolerance compared to the xylanase of SEQ ID NO: 3; and i) wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3; or ii) wherein the number of alterations is 1-20, e.g., 1-10 such as 1, 2, 3, 4, 5, 6, 7, 8, 9 or 10 alterations.

Paragraph [2]. The xylanase variant of paragraph 1, wherein the alteration at position 87 is a substitution.

Paragraph [3]. The xylanase variant of paragraph 2, wherein the alteration is a substitution with Tyr.

Paragraph [4]. The xylanase variant of paragraph 3, wherein the substitution is H87Y.

Paragraph [5]. The xylanase variant according to any of the paragraphs 1-4, wherein the xylanase inhibitor is a proteinaceous inhibitor derived from wheat or other cereals.

Paragraph [6]. The xylanase variant according to any of the preceding paragraphs, wherein the variant has at least 75%, more preferably at least 80%, more preferably at least 85%, even more preferably at least 90%, most preferably at least 95%, and even most preferably at least 100% of the xylanase activity of the polypeptide of SEQ ID NO: 3 comprising the H87Y substitution.

Paragraph [7]. The variant according to any of the preceding claims, wherein the variant has an increase in relative xylanase activity over the wild type xylanase of at least a factor 7×, particularly 8×, particularly 8.5× more particularly 9×, in the presence of wheat xylanase inhibitors, particularly XIP-1, in amounts that will reduce the wild type xylanase activity to less than 10%.

Paragraph [8]. A polynucleotide encoding the xylanase variant of any of paragraphs 1-7.

Paragraph [9]. A nucleic acid construct comprising the polynucleotide of paragraph 8.

Paragraph [10]. An expression vector comprising the polynucleotide of paragraph 8.

Paragraph [11]. A host cell comprising the polynucleotide of paragraph 8.

Paragraph [12]. A method of producing a xylanase variant, comprising: cultivating the host cell of paragraph 11 under conditions suitable for expression of the variant; and recovering the variant.

Paragraph [13]. A transgenic plant, plant part or plant cell comprising the polynucleotide of paragraph 8.

Paragraph [14]. A process of producing a fermentation product from starch-containing material comprising the steps of: (a) liquefying starch-containing material in the presence of an alpha amylase; (b) saccharifying the liquefied material; and (c) fermenting with a fermenting organism; wherein the xylanase variant of paragraphs 1-7 is present during step (a).

Paragraph [15]. A process of producing a syrup product from starch-containing material, comprising the step of: (a) blending the dry starch-containing material with water to form a mash, (b) liquefying starch-containing material in the presence of an alpha amylase; (c) saccharifying the liquefied material in the presence of a glucoamylase, wherein the xylanase variant of any of paragraphs 1-7 is present during step (a) and/or (b).

Paragraph [16]. The process of paragraphs 14 or 15, wherein the starch-containing material comprises wheat or barley.

Paragraph [17]. A process for producing a fermentation product, comprising:

(a) saccharifying a cellulosic or xylan-containing material with an enzyme composition in the presence of the polypeptide having xylanase activity of any of paragraphs 1-7;
(b) fermenting the saccharified cellulosic or xylan-containing material with one or more fermenting microorganisms to produce the fermentation product; and
(c) recovering the fermentation product from the fermentation.

Paragraph [18]. The process according to paragraphs 14 or 17, wherein the fermentation product is ethanol.

Paragraph [19]. A composition comprising the variant of any of paragraphs 1-7.

Paragraph [20]. The composition according to paragraph 19, further comprising an alpha-amylase, a protease, and a glucoamylase.

Paragraph [21]. A process for degrading a xylan containing material, comprising: treating the xylan material with an enzyme composition of paragraph 20.

Paragraph [22]. The process according to paragraph 21, wherein the composition further comprises one or more enzymes selected from the group consisting of an endoglucanase, a cellobiohydrolase, and a beta-glucosidase.

Paragraph [23]. A whole broth formulation or cell culture composition, comprising the variant of any of paragraphs 1-7. The present invention is further described by the following examples that should not be construed as limiting the scope of the invention.

EXAMPLES

Strain

*Aspergillus oryzae* strain MT3568 as disclosed in U.S. Patent Application No: US20110111453 was used as an expression host for the *Aspergillus fumigatus* GH10A xylanase and variants thereof.

Media and Reagents

AMG trace metals solution was composed of 14.3 g of $ZnSO_4 \cdot 7H_2O$, 2.5 g of $CuSO_4 \cdot 5H_2O$, 0.5 g of $NiCl_2 \cdot 6H_2O$, 13.8 g of $FeSO_4 \cdot 7H_2O$, 8.5 g of $MnSO_4 \cdot H_2O$, 3 g of citric acid, and deionized water to 1 liter.

MDU2BP medium (pH 5.0) was composed of 135 g of maltose, 3 g of $MgSO_4 \cdot 7H_2O$, 3 g of NaCl, 6 g of $K_2SO_4$, 36 g of $KH_2PO_4$, 21 g of yeast extract, 6 g of urea, 1.5 ml of AMG trace metals solution, and deionized water up to 1 liter.

PEG solution was composed of 6 g of polyethylene glycol 4000 (PEG 4000), 100 µl of 1 M Tris pH 7.5, 100 µl of 1 M $CaCl_2$, and deionized water to 10 ml.

2XYT agar plates were composed of 16 g of tryptone, 10 g of yeast extract, 5 g of NaCl, 15 g of Bacto agar, and deionized water to 1 liter.

2XYT+Amp agar plates were composed of 2XYT agar supplemented with 100 µg of ampicillin per ml.

Example 1

Construction of *Aspergillus fumigatus* GH10 xylanase variants

Variants of *Aspergillus fumigatus* GH10 xylanase (SEQ ID NO: 1) were constructed by performing a single site-directed mutagenesis reaction on pHyGe001 as described in U.S. Pat. No. 7,960,160) using a QUIKCHANGE® II XL Site-Directed Mutagenesis Kit (Stratagene, La Jolla, Calif., USA). Two mutagenic primers were designed to insert the desired mutation. The PCR was composed of 12.5 ng of each primer, approximately 10 ng of template plasmid, 1× QUIKCHANGE® Reaction Buffer (Stratagene, La Jolla, Calif., USA), 1 µl of QUIKCHANGE® II XL dNTP mix (Stratagene, La Jolla, Calif., USA), and 1 µl of 2.5 U/µl Pfu ULTRA™ enzyme (Stratagene, La Jolla, Calif., USA) in a final volume of 50 µl. The amplification reaction was performed using an EPPENDORF® MASTERCYCLER® thermal cycler (Eppendorf, Hauppauge, N.Y., USA) programmed for a 95° C. hot start; 1 cycle at 95° C. for 30 seconds; 16 cycles each at 95° C. for 30 seconds, 55° C. for 1 minute, and 68° C. for 9 minutes; and a 4° C. hold. One microliter of Dpn I was directly added to the amplification reaction and incubated at 37° C. for 1 hour. A 2 µl volume of the Dpn I digested reaction was used to transform *E. coli* ONE SHOT® TOP10 Ultracompetent Cells (Life Technologies, Grand Island, N.Y., USA) according to the manufacturer's instructions. *E. coli* transformants were selected on 2XYT+Amp agar plates. Plasmid DNA from several of the resulting *E. coli* transformants was prepared using a BIOROBOT® 9600 (QIAGEN Inc., Valencia, Calif., USA). The insert was confirmed by DNA sequencing using a Model 3130xL Genetic Analyzer (Applied Biosystems, Life Technologies, Grand Island, N.Y., USA) and dye-terminator chemistry from a BIGDYE® Terminator v3.1 Cycle Sequencing Kit (Applied Biosystems, Life Technologies, Grand Island, N.Y., USA). For each reaction, one of the clones with the desired mutation was chosen. The primers used in the reaction to generate a specific *Aspergillus fumigatus* GH10 variant with the H87Y mutation are shown in Table 1.

TABLE 1

| Plasmid | Mutation | Parent Plasmid | Oligo ID # | Primer Sequence |
|---|---|---|---|---|
| pMaWo142-24 | H87Y | pHyGe001 | 1200245 | CGATGCCATACTCTGGTCTGGTACA GTCAGCTACCGAACTGGGGT (SEQ ID NO: 5) |
| | | | 1200246 | ACCCCAGTTCGGTAGCTGACTGTA CCAGACCAGAGTATGGCATCG (SEQ ID NO: 6) |

Example 2

Expression of the *Aspergillus fumigatus* GH10 Xylanase Variants in *Aspergillus oryzae* MT3568

*Aspergillus oryzae* MT3568 protoplasts were prepared according to the method of Christensen et al., 1988, *Bio/Technology* 6: 1419-1422, and transformed with 5 µg of each of the expression vector. The transformations yielded about 1-10 transformants for each vector. Up to four transformants for each transformation were isolated to individual PDA plates.

Confluent PDA plates of the transformants were washed with 8 ml of 0.01% TWEEN® 20 and inoculated separately into 1 ml of MDU2BP medium in sterile 24 well tissue culture plates and incubated at 34° C. Four days after incubation, 20 μl of harvested broth from each culture was analyzed using 8-16% Tris-Glycine SDS-PAGE gels (Invitrogen, Carlsbad, Calif., USA) according to the manufacturer's instructions. SDS-PAGE profiles of the cultures showed that several transformants had a new major band of approximately 45 kDa.

A confluent plate of one transformant for each transformation (grown on PDA) was washed with 8 ml of 0.01% TWEEN® 20 and inoculated into 125 ml glass baffled shake flasks containing 25 ml of MDU2BP medium and incubated at 34° C. with agitation at 225 rpm to generate broths for characterization of the variants. The flasks were harvested on day 4 and filtered using a 0.22 μm GP Express plus Membrane (Millipore, Bedford, Mass., USA).

Example 3

Thermoactivity of GH10 Xylanases from *Aspergillus aculeatus* and *Aspergillus fumigatus*

The *Aspergillus fumigatus* GH10 xylanase was expressed from *Aspergillus oryzae* MT5668 as described in U.S. Patent Application US20110111453. The *Aspergillus aculeatus* xylanase tested here is a commercial product named Shearzyme 500 from Novozymes (SEQ ID NO: 4). Both enzymes were tested for activity on wheat arabinoxylan at temperatures ranging from about 70-92° C. as described below.

The substrate was prepared by first wetting 0.5 g of medium viscosity wheat arabinoxylan (Megazyme, Produce Code PWAXYM) with 4 mL of ethanol in a beaker and then adding 50 mL of 100 mM sodium citrate, pH 5.0. The substrate was stirred with gentle heating on a hot plate until the substrate was fully dissolved. A DNS solution was prepared by adding 20 g NaOH, 4 g phenol and 1 g of sodium metabisulfilte to 900 mL of water in a fume hood. Samples were diluted to an approximate final xylanase protein concentration of 1 μg/mL in citrate buffer in a glass test tube.

50 μL of each diluted enzyme was transferred to all wells in three successive rows in a 96 well PCR plate. 50 μL of 20, 10, 5, 2.5, 1.2 and 0.6 mM xylose standards, made up in citrate buffer, were added to wells 1 to 6 in row A and 50 μL of citrate buffer was added to wells 7 to 12 in row A of the PCR plate. 50 μL of substrate was added to all wells and the PCR plate transferred to a thermal cycler programmed for a 70-92° C. temperature gradient and incubated for 1 h. 80 μL of DNS was added to each well and the plate incubated at 95° C. for 5 min. The plate was then centrifuged at 1000×g for 1 min. 130 μL from each well was transferred to the corresponding well in a microtitre plate and the absorbance measured at 560 nm. The slope (m) and y-intercept (b) of the absorbance versus xylose concentration data were analyzed by linear regression using methods known by one of ordinary skill in the art. The xylose concentration in each sample well was calculated using the equation below:

$$[xylose(mM)] = \frac{Absorbance(sample) - b}{m}$$

Xylanase activity was then calculated in pmol xylose equivalents produced per minute using the equation below:

$$Xylanase\ Activity\left(\frac{\mu mol}{min}\right) = xylose\left(\frac{mmol}{L}\right) \times \frac{1000\ \mu mol}{mmol} \times 50\ \mu L \times \frac{1\ L}{10^6\ \mu L} \times \frac{1}{60\ min}$$

Relative enzyme activity values were calculated by dividing the xylanase activity at each temperature by the maximum xylanase activity measured for each enzyme. These values are shown plotted as a function of temperature in FIG. 1. The highest activity of the AacuGH10 was measured at 70° C. while the highest activity of the AfumGH10 was measured at 76° C. These results demonstrate that the *Aspergillus fumigatus* xylanase is more active at higher temperatures than *Aspergillus aculeatus* xylanase.

Example 4

Inhibitor Production

Proteinaceous inhibitors were extracted from wheat flour using a method adapted from McLauchlan et al. (A novel class of protein from wheat which inhibits xylanases. (1999), Biochem. J., 338: 441-446). Briefly, 10 g of wheat flour was suspended in 50 g of distilled, deionized water and mixed at room temperature for 30 min. During this step the proteinaceous inhibitors dissolve while insoluble fibers, such as xylan and cellulose, and starch remain largely insoluble. The suspension was then filtered under vacuum to separate residual insoluble components of the wheat flour from the proteinaceous inhibitors in the filtrate. The filtrate was collected and washed with 3 volumes of 50 mM sodium citrate, pH 5.0 using Vivaspin 20 spin columns with a 5,000 MWCO (VIVAproducts, catalogue #28-9323-59). The retentate was used for subsequent inhibition assays. Note that the procedure used here does not separate different classes of wheat inhibitors (XIP1, TAXI, etc.).

Example 5

Sensitivity of GH10 Xylanases from *Aspergillus aculeatus* and *Aspergillus fumigatus* to Wheat-Derived Inhibitors Five ½ serial dilutions of the wheat inhibitor preparation of Example 4 were prepared in test tubes by combining 2 mL of wheat filtrate (or previous dilution) and 2 mL of citrate buffer. The inhibitor preparation and the serial dilutions thereof were transferred to rows B to G of a PCR plate as shown below.

Plate layout of wheat inhibitor dilutions and enzyme. Dilutions 1-6 refer to increasing dilutions (lower relative concentrations) of the wheat inhibitors.

|   | 1 | 2 | 3 | 4 | 5 | 6 |
|---|---|---|---|---|---|---|
| A |   |   |   |   |   |   |
| B | Sample1 Dil. 1 | Sample1 Dil. 1 | Sample1 Dil. 1 | Sample2 Dil. 1 | Sample2 Dil. 1 | Sample2 Dil. 1 |
| C | Sample1 Dil. 2 | Sample1 Dil. 2 | Sample1 Dil. 2 | Sample2 Dil. 2 | Sample2 Dil. 2 | Sample2 Dil. 2 |
| D | Sample1 Dil. 3 | Sample1 Dil. 3 | Sample1 Dil. 3 | Sample2 Dil. 3 | Sample2 Dil. 3 | Sample2 Dil. 3 |
| E | Sample1 Dil. 4 | Sample1 Dil. 4 | Sample1 Dil. 4 | Sample2 Dil. 4 | Sample2 Dil. 4 | Sample2 Dil. 4 |
| F | Sample1 Dil. 5 | Sample1 Dil. 5 | Sample1 Dil. 5 | Sample2 Dil. 5 | Sample2 Dil. 5 | Sample2 Dil. 5 |
| G | Sample1 Dil. 6 | Sample1 Dil. 6 | Sample1 Dil. 6 | Sample2 Dil. 6 | Sample2 Dil. 6 | Sample2 Dil. 6 |
| H | Sample1 Blank | Sample1 Blank | Sample1 Blank | Sample2 Blank | Sample2 Blank | Sample2 Blank |

50 μL of citrate buffer was transferred to row H. 50 μL of each enzyme diluted as per Example 1 was added to rows B to H in three consecutive columns in the PCR plate and the PCR plate incubated in a thermal cycler at 50° C. for 30 min. The relative inhibitor concentrations after addition of enzyme in rows B to G were 0.500, 0.250, 0.125, 0.0625, 0.03125 and 0.01563. 50 µL from each well was then transferred to a new PCR plate and xylanase activity measured in each well at 50° C. as otherwise described in Example 3.

Figure 2:
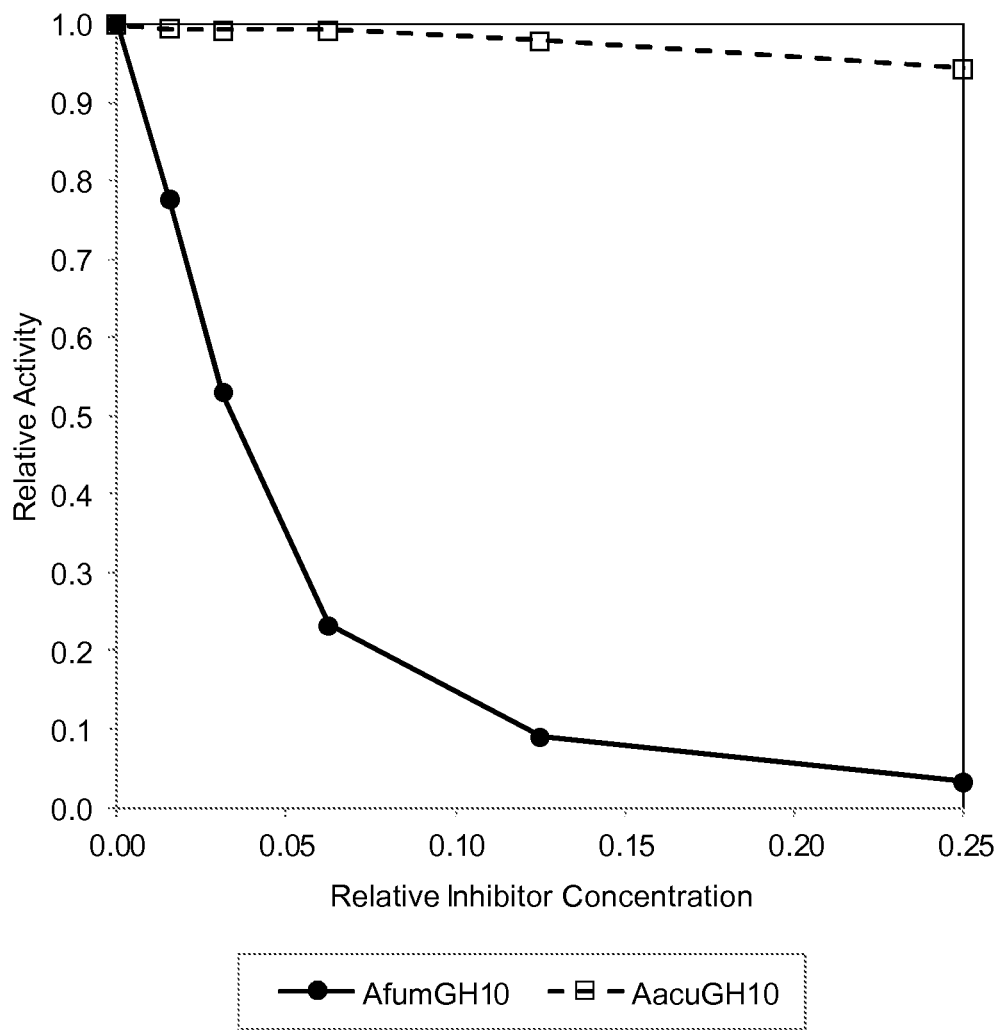
FIG. 2 shows that the wild-type AfumGH10 is markedly affected by wheat-derived inhibitors while effects on the AacuGH10 were negligible under these conditions. Xylanases were pre-incubated with various dilutions of wheat-derived inhibitors for 30 min at room temperature and then tested for activity on wheat arabinoxylan at 50° C., pH 5.0.

Apparent xylanase activity plotted as a function of relative inhibitor concentration is shown in FIG. 2 for relative inhibitor concentrations less than or equal to 0.250. Changes in xylose release measured upon incubation of the *Aspergillus aculeatus* GH10 xylanase with increasing wheat inhibitor concentrations were negligible indicating it is tolerant to wheat-derived inhibitors, as has been reported previously (Flatman et al., Interactions defining the specificity between fungal xylanases and the xylanase-inhibiting protein XIP-I from wheat. Biochem. J. (2002); 365: 773-781; Juge, N. et al., XIP-I, a xylanase inhibitor protein from wheat: a novel protein function. Biochem Biophys Acta, (2003), 1696: 203-211; Gebruers, K. et al., Properties of TAXI-type endoxylanase inhibitors. Biochem Biophys Acta, (2003), 1696: 213-221; Goesaert et al., Occurrence of proteinaceous endoxylanase inhibitors in cereals. Biochem Biophys Acta., (2003), 1696: 193-202). In contrast, the activity of the *Aspergillus fumigatus* GH10 xylanase decreased markedly with increasing wheat inhibitor concentrations indicating it was strongly inhibited.

Example 6

Figure 3:
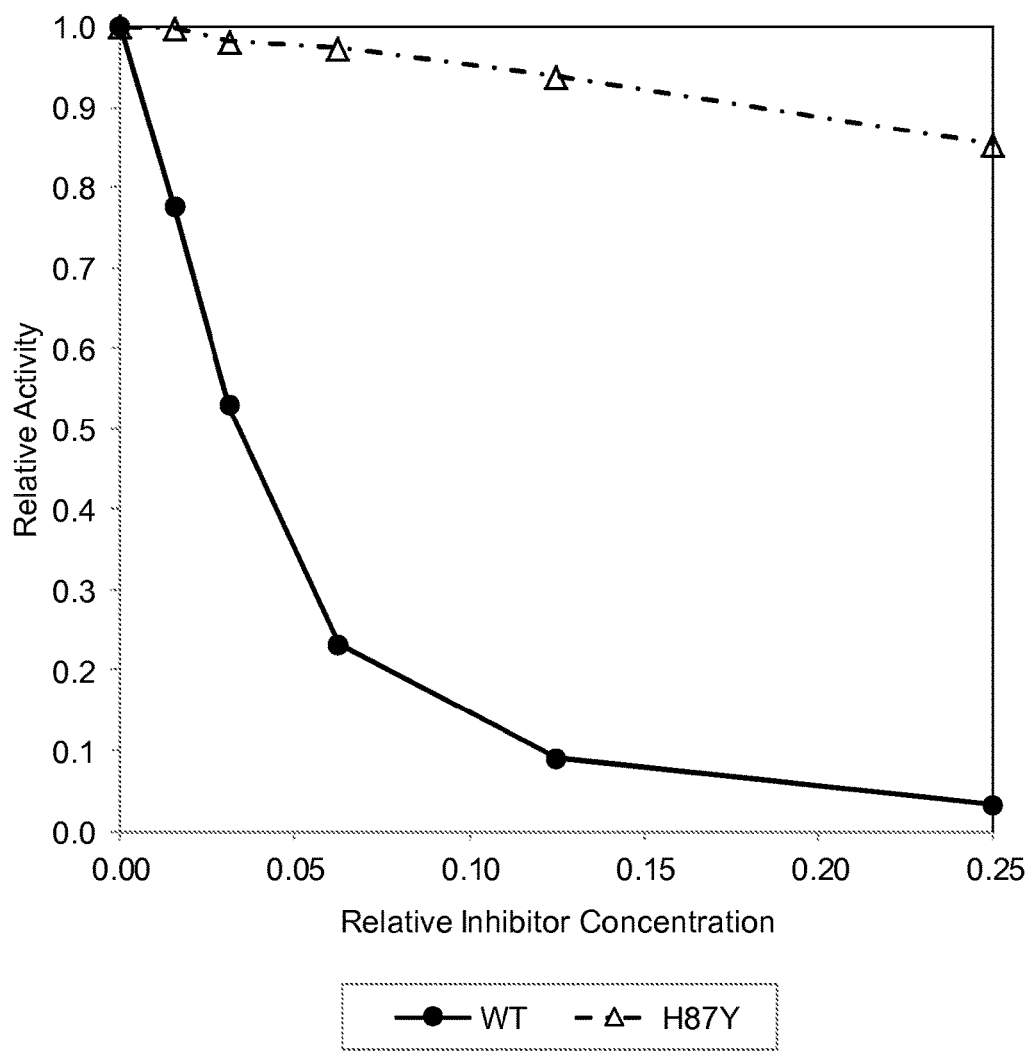
FIG. 3 shows that the H87Y variant is significantly more tolerant to wheat-derived inhibitors than is wild-type AfumGH10. Enzymes were first pre-incubated with several dilutions of a wheat inhibitor preparation and then assayed for residual activity on wheat arabinoxylan.

Assaying the Inhibitor Sensitivity and Thermoactivity of the *Aspergillus fumigatus* GH10 Xylanase Variant Variants of the *Aspergillus fumigatus* GH10 and the wild-type were tested in the inhibitor assay described in Example 5. The H87Y variant was markedly more inhibitor tolerant than the wild-type and was similar in this regard to the *Aspergillus aculeatus* GH10 (FIG. 3).

Figure 4:
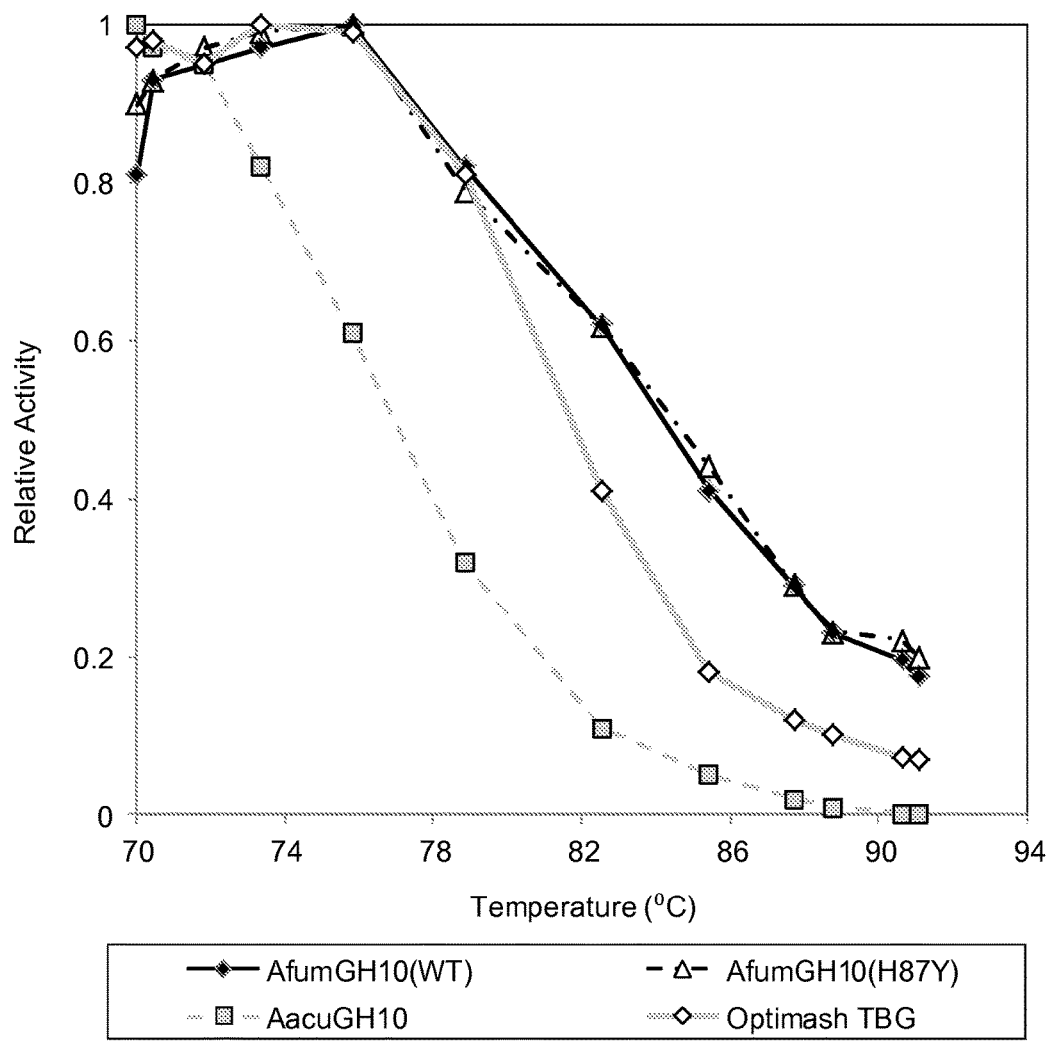
FIG. 4 demonstrates that the H87Y mutation confers no ill effects on the thermostability of AfumGH10. Enzymes were incubated with wheat arabinoxylan for 1 h at the temperatures indicated and then xylose concentrations were measured using a reducing sugar assay. This figure also shows that the AfumGH10, both the wild-type and the H87Y variant, has higher thermoactivity than does the xylanase activity in the commercial grain processing enzyme Optimash TBG.

The *Aspergillus fumigatus* GH10 (H87Y) xylanase variant was also tested in the thermoactivity assay described in Example 4. In this case, Optimash TBG, a high temperature grain processing product from DuPont was also included for reference. Furthermore, both the *Aspergillus fumigatus* GH10 xylanase variant and the wild-type have greater thermoactivity than the xylanases in Optimash TBG (FIG. 4).

The invention claimed is:

1. A xylanase variant, comprising an alteration at least at one position corresponding to position 87 of the polypeptide of SEQ ID NO: 3, wherein the variant has xylanase activity and has increased xylanase inhibitor tolerance compared to the xylanase of SEQ ID NO: 3; and
   i) wherein the variant has at least 85% but less than 100% sequence identity to the polypeptide of SEQ ID NO: 3.

2. The xylanase variant of claim 1, wherein the alteration at position 87 is a substitution.

3. The xylanase variant of claim 2, wherein the alteration is a substitution with Tyr.

4. The xylanase variant of claim 3, wherein the substitution is H87Y.

5. The xylanase variant according to claim 1, wherein the xylanase inhibitor is a proteinaceous inhibitor derived from wheat or other cereals.

6. The xylanase variant according to claim 1, wherein the variant has at least 75% of the xylanase activity of the polypeptide of SEQ ID NO: 3 comprising the H87Y substitution.

7. The variant according to claim 1, wherein the variant has an increase in relative xylanase activity over the wild type xylanase of at least a factor 7× in the presence of wheat xylanase inhibitors in amounts that will reduce the wild type xylanase activity to less than 10%.

8. A process of producing a fermentation product from starch-containing material comprising the steps of: (a) liquefying starch-containing material in the presence of an alpha amylase; (b) saccharifying the liquefied material; and (c) fermenting with a fermenting organism; wherein the xylanase variant of claim 1 is present during step (a).

9. A process of producing a syrup product from starch-containing material, comprising the step of: (a) blending the dry starch-containing material with water to form a mash, (b) liquefying starch-containing material in the presence of an alpha amylase; (c) saccharifying the liquefied material in the presence of a glucoamylase, wherein the xylanase variant of claim 1 is present during step (a) and/or (b).

10. The process of claim 8, wherein the starch-containing material comprises wheat or barley.

11. A process for producing a fermentation product, comprising:
   (a) saccharifying a cellulosic or xylan-containing material with an enzyme composition in the presence of the polypeptide having xylanase activity of claim 1;
   (b) fermenting the saccharified cellulosic or xylan-containing material with one or more fermenting microorganisms to produce the fermentation product; and
   (c) recovering the fermentation product from the fermentation.

12. The process according to claim 8, wherein the fermentation product is ethanol.

13. A composition comprising the variant of claim 1.

14. The composition according to claim 13, further comprising an alpha-amylase, and a protease, and optionally a glucoamylase.

15. A process for degrading a xylan containing material, comprising: treating the xylan material with an enzyme composition of claim 13.

16. The process according to claim 15, wherein the composition further comprises one or more enzymes selected from the group consisting of an endoglucanase, a cellobiohydrolase, and a beta-glucosidase.

17. A whole broth formulation or cell culture composition, comprising the variant of claim 1.

* * * * *

SEQUENCE LISTING

<160> NUMBER OF SEQ ID NOS: 6

<210> SEQ ID NO 1
<211> LENGTH: 1194
<212> TYPE: DNA
<213> ORGANISM: Aspergillus fumigatus

<400> SEQUENCE: 1

```
atggtccatc tatcttcatt ggcagcagcc ctggctgctc tgcctcttgt atatggagct      60
ggcctgaaca cagcagccaa agccaaagga ctaaagtact ttggttccgc cacggacaat     120
ccagagctca cggactctgc gtatgtcgcg caactgagca caccgatga ttttggtcaa     180 atcacacccg gaaactccat gaagtgggat gccaccgagc cttctcagaa ttcttttcg     240 ttcgcaaatg gagacgccgt ggtcaatctg gcgaacaaga atggccagct gatgcgatgc     300
catactctgg tctggcacag tcagctaccg aactgggtct ctagcgggtc atggaccaat     360
gcgacccttt tggcggccat gaagaatcat atcaccaatg tggttactca ctacaagggg     420
aagtgctacg cctgggatgt tgtcaatgaa gcccgaacg aggacggtac tttccgtaac     480
tctgtcttct accagatcat cggcccagca tacattccta ttgcgttcgc cacggctgct     540
gccgcagatc ccgacgtgaa actctactac aacgactaca acattgaata ctcaggcgcc     600
aaagcgactg ctgcgcagaa tatcgtcaag atgatcaagg cctacggcgc gaagatcgac     660
ggcgtcggcc tccaggcaca ctttatcgtc ggcagcactc cgagtcaatc ggatctgacg     720
accgtcttga agggctacac tgctctcggc gttgaggtgg cctataccga acttgacatc     780
cgcatgcagc tgccctcgac cgccgcaaag ctggcccagc agtccactga cttccaaggc     840
gtggccgcag catgcgttag caccactggc tgcgtgggtg tcactatctg ggactggacc     900
gacaagtact cctgggtccc cagcgtgttc caaggctacg gcgccccatt gccttgggat     960
gagaactatg tgaagaagcc agcgtacgat ggcctgatgg cgggtcttgg agcaagcggc    1020
tccggcacca caacgaccac tactactact tctactacga caggaggtac ggaccctact    1080
ggagtcgctc agaaatgggg acagtgtggc ggtattggct ggaccgggcc aacaacttgt    1140
gtcagtggta ccacttgcca aaagctgaat gactggtact cacagtgcct gtaa          1194
```

```
<210> SEQ ID NO 2
<211> LENGTH: 397
<212> TYPE: PRT
<213> ORGANISM: Aspergillus fumigatus

<400> SEQUENCE: 2

Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
    195                 200                 205

Val Lys Met Ile Lys Ala Tyr Gly Ala Lys Ile Asp Gly Val Gly Leu
210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365
```

```
Cys Gly Gly Ile Gly Trp Thr Gly Pro Thr Thr Cys Val Ser Gly Thr
370                 375                 380

Thr Cys Gln Lys Leu Asn Asp Trp Tyr Ser Gln Cys Leu
385                 390                 395
```

<210> SEQ ID NO 3
<211> LENGTH: 378
<212> TYPE: PRT
<213> ORGANISM: Aspergillus fumigatus

<400> SEQUENCE: 3

```
Ala Gly Leu Asn Thr Ala Ala Lys Ala Lys Gly Leu Lys Tyr Phe Gly
1               5                   10                  15

Ser Ala Thr Asp Asn Pro Glu Leu Thr Asp Ser Ala Tyr Val Ala Gln
                20                  25                  30

Leu Ser Asn Thr Asp Asp Phe Gly Gln Ile Thr Pro Gly Asn Ser Met
            35                  40                  45

Lys Trp Asp Ala Thr Glu Pro Ser Gln Asn Ser Phe Ser Phe Ala Asn
50                  55                  60

Gly Asp Ala Val Val Asn Leu Ala Asn Lys Asn Gly Gln Leu Met Arg
65                  70                  75                  80

Cys His Thr Leu Val Trp His Ser Gln Leu Pro Asn Trp Val Ser Ser
                85                  90                  95

Gly Ser Trp Thr Asn Ala Thr Leu Leu Ala Ala Met Lys Asn His Ile
            100                 105                 110

Thr Asn Val Val Thr His Tyr Lys Gly Lys Cys Tyr Ala Trp Asp Val
        115                 120                 125

Val Asn Glu Ala Leu Asn Glu Asp Gly Thr Phe Arg Asn Ser Val Phe
130                 135                 140

Tyr Gln Ile Ile Gly Pro Ala Tyr Ile Pro Ile Ala Phe Ala Thr Ala
145                 150                 155                 160

Ala Ala Ala Asp Pro Asp Val Lys Leu Tyr Tyr Asn Asp Tyr Asn Ile
                165                 170                 175

Glu Tyr Ser Gly Ala Lys Ala Thr Ala Ala Gln Asn Ile Val Lys Met
            180                 185                 190

Ile Lys Ala Tyr Gly Ala Lys Ile Asp Gly Val Gly Leu Gln Ala His
        195                 200                 205

Phe Ile Val Gly Ser Thr Pro Ser Gln Ser Asp Leu Thr Thr Val Leu
210                 215                 220

Lys Gly Tyr Thr Ala Leu Gly Val Glu Val Ala Tyr Thr Glu Leu Asp
225                 230                 235                 240

Ile Arg Met Gln Leu Pro Ser Thr Ala Ala Lys Leu Ala Gln Gln Ser
                245                 250                 255

Thr Asp Phe Gln Gly Val Ala Ala Cys Val Ser Thr Thr Gly Cys
            260                 265                 270

Val Gly Val Thr Ile Trp Asp Trp Thr Asp Lys Tyr Ser Trp Val Pro
        275                 280                 285

Ser Val Phe Gln Gly Tyr Gly Ala Pro Leu Pro Trp Asp Glu Asn Tyr
290                 295                 300

Val Lys Lys Pro Ala Tyr Asp Gly Leu Met Ala Gly Leu Gly Ala Ser
305                 310                 315                 320

Gly Ser Gly Thr Thr Thr Thr Thr Thr Thr Ser Thr Thr Thr Gly
                325                 330                 335

Gly Thr Asp Pro Thr Gly Val Ala Gln Lys Trp Gly Gln Cys Gly Gly
            340                 345                 350
```

```
Ile Gly Trp Thr Gly Pro Thr Thr Cys Val Ser Gly Thr Cys Gln
        355                 360                 365

Lys Leu Asn Asp Trp Tyr Ser Gln Cys Leu
    370                 375

<210> SEQ ID NO 4
<211> LENGTH: 406
<212> TYPE: PRT
<213> ORGANISM: Aspergillus aculeatus

<400> SEQUENCE: 4

Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
        35                  40                  45

Ile Pro Tyr Val Thr Gln Leu Asn Asn Thr Ala Asp Phe Gly Gln Ile
    50                  55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
        115                 120                 125

Ala Leu Lys Asn His Ile Thr Asn Val Val Ser His Tyr Lys Gly Lys
    130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
            180                 185                 190

Tyr Asn Asp Tyr Asn Leu Glu Tyr Gly Gly Ala Lys Ala Ala Ser Ala
        195                 200                 205

Arg Ala Ile Val Gln Leu Val Lys Asn Ala Gly Ala Lys Ile Asp Gly
    210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
        275                 280                 285

Val Gln Thr Thr Gly Cys Val Gly Phe Thr Ile Trp Asp Trp Thr Asp
    290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
            340                 345                 350
```

```
Thr Ala Thr Gly Lys Thr Thr Thr Thr Thr Gly Ala Thr Ser Thr
            355                 360                 365

Gly Thr Thr Ala Ala His Trp Gly Gln Cys Gly Gly Leu Asn Trp Ser
    370                 375                 380

Gly Pro Thr Ala Cys Ala Thr Gly Tyr Thr Cys Thr Tyr Val Asn Asp
385                 390                 395                 400

Tyr Tyr Ser Gln Cys Leu
                405

<210> SEQ ID NO 5
<211> LENGTH: 45
<212> TYPE: DNA
<213> ORGANISM: Artificial
<220> FEATURE:
<223> OTHER INFORMATION: PCR primer

<400> SEQUENCE: 5
cgatgccata ctctggtctg gtacagtcag ctaccgaact ggggt              45

<210> SEQ ID NO 6
<211> LENGTH: 45
<212> TYPE: DNA
<213> ORGANISM: Artificial
<220> FEATURE:
<223> OTHER INFORMATION: PCR primer

<400> SEQUENCE: 6
accccagttc ggtagctgac tgtaccagac cagagtatgg catcg              45
```